US009428795B2

United States Patent
Kajiyama et al.

(10) Patent No.: US 9,428,795 B2
(45) Date of Patent: Aug. 30, 2016

(54) PLANT TISSUE SAMPLING METHOD AND PLANT GENE ANALYSIS METHOD

(71) Applicant: Hitachi, Ltd., Chiyoda-ku, Tokyo (JP)

(72) Inventors: Tomoharu Kajiyama, Tokyo (JP); Hideki Kambara, Tokyo (JP); Toru Habu, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 117 days.

(21) Appl. No.: 14/380,570

(22) PCT Filed: Dec. 18, 2012

(86) PCT No.: PCT/JP2012/082732
§ 371 (c)(1),
(2) Date: Aug. 22, 2014

(87) PCT Pub. No.: WO2013/125141
PCT Pub. Date: Aug. 29, 2013

(65) Prior Publication Data
US 2015/0018243 A1   Jan. 15, 2015

(30) Foreign Application Priority Data
Feb. 23, 2012   (JP) ................................. 2012-037593

(51) Int. Cl.
*C12Q 1/68*   (2006.01)
*C12M 1/26*   (2006.01)

(52) U.S. Cl.
CPC ............. *C12Q 1/6806* (2013.01); *C12M 33/04* (2013.01)

(58) Field of Classification Search
CPC ............................ C12Q 1/6806; C12M 33/04

USPC ........................ 506/9, 30; 435/6.11
See application file for complete search history.

(56) References Cited

U.S. PATENT DOCUMENTS

2007/0281313 A1   12/2007 Taniguchi et al.

FOREIGN PATENT DOCUMENTS

JP   2007-319028 A   12/2007

OTHER PUBLICATIONS

Aharoni et al. (Plant Molecular Biology, 2001, 48, pp. 99-118).*
Hosokawa et al., Journal of Virological Methods, 2006, 131, pp. 28-33.*
Shiokai et al. "Leaf-punch method to prepare a large number of PCR templates from plants for SNP analysis" Molecular Breeding, 2009, vol. 23, pp. 329-336.
International Search Report (PCT/ISA/210) dated Feb. 26, 2013 with English translation (five pages).
Japanese-language Written Opinion (PCT/ISA/237) dated Feb. 26, 2013 (four pages).

(Continued)

*Primary Examiner* — Larry Riggs
*Assistant Examiner* — Karla Dines
(74) *Attorney, Agent, or Firm* — Crowell & Moring LLP

(57) ABSTRACT

To provide a means and a method of quickly sampling a tissue fragment from a plant tissue, quickly preserving a gene expression state within the tissue fragment, and comprehensively analyzing the gene expression state. The present invention relates to a method of sampling a plant tissue section, comprising: inserting a first gel layer into a needle; arranging a plant tissue on a second gel layer; and passing the needle through the plant tissue together with the second gel layer, and sampling a section of the plant tissue in the needle.

15 Claims, 16 Drawing Sheets

(56) References Cited

OTHER PUBLICATIONS

Brandt et al. "A Simple, Chisel-Assisted Mechanical Microdissection System for Harvesting Homogenous Plant Tissue Suitable for the Analysis of Nucleic Acids and Proteins" Plant Molecular Biology Reporter, Dec. 2003, pp. 417-427, vol. 21, International Society for Plant Molecular Biology.

Jost et al. "Magnetic quantitative reverse transcription PCR: A high-throughput method for mRNA extraction and quantitative reverse transcription Pcr" Short Technical Reports, Aug. 2007, pp. 206-211, vol. 43, Issue 2, BioTechniques, The Australian National University; Canberra, Australia.

Terpitz et al. "Isolation of guard cells from fresh epidermis using a piezo-power microdissection system with vibration-attenuated needles" Benchmarks, Jan. 2010, pp. 68-70, vol. 48, Issue 1, BioTechniques.

Taniguchi et al. "Quantitative analysis of gene expression in a single cell by qPCR" Brief Communications, Jul. 2009, 23 pages, vol. 6, Issue 7, Nature Methods.

\* cited by examiner (a)            (b)

```
                         SEQUENCE LISTING

<160> NUMBER OF SEQ ID NOS: 5

<210> SEQ ID NO 1
<211> LENGTH: 17
<212> TYPE: DNA
<213> ORGANISM: Artificial
<220> FEATURE:
<223> OTHER INFORMATION: primer

<400> SEQUENCE: 1
caaggcacgg acgctac                                                    17

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
gaaacatcac aggcaataac a                                               21

<210> SEQ ID NO 3
<211> LENGTH: 24
<212> TYPE: DNA
<213> ORGANISM: Artificial
<220> FEATURE:
<223> OTHER INFORMATION: primer

<400> SEQUENCE: 3
tgaatatcaa caggaggaag agta                                            24

<210> SEQ ID NO 4
<211> LENGTH: 26
<212> TYPE: DNA
<213> ORGANISM: Artificial
<220> FEATURE:
<223> OTHER INFORMATION: primer

<400> SEQUENCE: 4
gtgttccttt taaaaaaaag aaaagt                                          26

<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
tgtttttgtt tttaaagcag ttata                                           25
```

PLANT TISSUE SAMPLING METHOD AND PLANT GENE ANALYSIS METHOD

BACKGROUND OF THE INVENTION

1. Field of the Invention

The present invention relates to a method and a system for sampling a section from a plant tissue. The present invention also relates to a gene analysis method for a plant tissue section, and more particularly, to a gene expression analysis method for a plant tissue with cell walls and vacuoles.

2. Background Art

A technique has been reported in which a micro site of a plant tissue is sampled by using a needle or the like, and substances such as genes and proteins expressed in the sampled object are analyzed (Non Patent Documents 1 and 3). In the technique, a plant tissue sliced by using a microtome is targeted, and a tissue fragment is separated and collected by a needle or a tip vibrated by a piezoelectric element under microscopy. Also, in the technique, genes in the collected section are subjected to cDNA synthesis by reverse transcription.

Also, as a cDNA library synthesis technique for expressed genes in a plant tissue, a cDNA synthesis technique has been disclosed in which a poly(T) probe fixed onto beads is used as a template (Non Patent Document 2). The technique discloses that cDNA is synthesized on beads by using a sample crushed at liquid nitrogen temperature.

Also, in an example using an animal tissue, as a quantitative PCR analysis technique using cDNA on beads, a gene analysis method has been developed in which a cDNA library where a gene obtained from a cell is used as a template is synthesized on a microcarrier such as magnetic beads, quantitative PCR regarding a first gene is performed by using the cDNA library, and the above cDNA library is then washed and repetitively used for quantitative analysis regarding second and third genes (Patent Document 1). By the technique, quantitative analysis of a plurality of types of genes in a single cell is achieved (Non Patent Document 4).

PRIOR ART DOCUMENTS

Patent Documents

Patent Document 1: JP Patent Publication No. 2007-319028 A

Non-Patent Documents

Non Patent Document 1: Brandt, S. et al., Plant Molecular Biology Reporter 21:417-427 (2003)
Non Patent Document 2: Jost, R. et al., Bio Techniques 43:206-211 (2007)
Non Patent Document 3: Terpitz, U. et al., Bio Techniques 48:68-70 (2010)
Non Patent Document 4: Taniguchi, K. et al., Nature Methods 6:503-506 (2009)

SUMMARY OF INVENTION

Problem to be Solved by the Invention

The present inventors conducted a study to consider a response of plants to environmental stimuli as a change in gene expression. Specifically, the present inventors studied how gene expression differed depending on a difference in site of an individual plant or a difference in spatial location when an external stimulus was applied to a plant. In the study, the following objects were examined.

(1) A tissue section having a certain volume is sampled from a plurality of sites in an individual plant, to which a stimulus is applied, quickly, ideally within 5 minutes, in a state in which application of other various stimuli is eliminated as much as possible.

(2) Since a "dissection" stimulus, which is a large physical stimulus, is applied to the individual plant at the time of sampling, a gene expression state is preserved (fixed) quickly, ideally within 1 minute, after the sampling.

(3) The sampled section preferably has a micro size, and, based on a demand of spatial resolution of a gene distribution to be studied, has a size equal to or less than 0.5 mm square.

(4) Even when the sampled section has a micro size, genes in the tissue section can be comprehensively analyzed.

(5) To this end, a plurality of types of genes can be comprehensively subjected to cDNA synthesis.

(6) To enable analysis of a gene having a low expression level, the recovery rate (the cDNA synthesis rate) of genes in the tissue section is 10% or more.

(7) The sections are sampled from a plurality of sites in the same individual.

However, it has been found that the above objects cannot be achieved by the conventional techniques. First, since a lot of preparations are required for sampling, it is impossible to collect tissue sections from a plurality of sites in the same individual within 5 minutes after applying a stimulus. Also, since there are too many various stimuli during sampling of the tissue section, it is expected that gene expression is disturbed. Moreover, no specific technique has been disclosed for a process from dissection to preservation of a gene expression state, so that the gene expression state cannot be quickly preserved. Thus, vacuoles in cells are destroyed by the influence of the dissection stimulus, and gene degradation proceeds by the action of a gene degradation enzyme in the vacuoles. Therefore, an expression state of a target gene(s) cannot be analyzed. Also, a gene extraction technique for a tissue fragment has not been disclosed at all. Specifically, a method of destroying cell walls of cells in a section, and subjecting every gene in cytoplasm to cDNA synthesis has not been disclosed. By the conventional methods, there is a large loss in gene recovery from a tissue fragment.

Thus, an object of the present invention is to provide a means and a method of quickly sampling a tissue fragment from a plant tissue, preferably, from a plurality of sites in a plant tissue, quickly preserving a gene expression state within the tissue fragment, and comprehensively analyzing the gene expression state.

Means for Solving the Problem

As a result of earnest study for achieving the above object, the present inventors found that the above object can be achieved by part or all of the following method, and arrived at the present invention.

(1) To optionally select one portion of a tissue of a plant body and quickly sample the portion, the plant tissue was sampled by a sampling needle. Specifically, a tissue sampling needle using a small tube of 27 gauges or 31 gauges was developed, and a method of sampling a section from a plurality of sites in the same individual at the same time was developed. Also, to quickly preserve a gene expression state, the temperature of the sampled section was quickly lowered to below the freezing point. As a method therefor, pure water, or a solution containing an inhibitor for a gene degradation enzyme was prepared as a liquid droplet, the sampled section was transferred into the liquid droplet, and the liquid droplet was cooled to liquid nitrogen temperature. Here, to surely transfer the tissue fragment from the needle to the liquid droplet, it is preferable to provide the needle with a syringe structure, and push out the tissue in the needle by a plunger. Since the tissue is damaged by contact with the needle at this point, it is necessary to previously protect the sampled section by a gel layer such as a gel or a polymer, as a means for preventing the damage. When gene immobilization or cDNA synthesis (reverse transcription reaction) as described below is performed, the gel layer such as a gel or a polymer should be a material that does not inhibit such reactions. By protecting the tissue by the gel layers, quickly transferring the section into the liquid droplet, and cooling the liquid droplet to the liquid nitrogen temperature, a process from the dissection to the cooling was performed within 1 minute.

(2) Cooling the liquid droplet containing the tissue of the tissue fragment to below the freezing point was effective in completely destroying cells in the tissue. When a physical force was applied by a pestle or the like in a state in which the liquid droplet is frozen below the freezing point, all the cellular tissues were completely homogenized, and cell content could be extracted to the outside of cell walls. However, in order to prevent a decrease in a gene recovery rate due to genes adhering to the surface of the pestle, (i) the surface of a tube was previously coated with a hydrophilic polymer so as to reduce adhesion of genes to a homogenizing tool such as the pestle, (ii) a technique of subjecting the tube together with the pestle to centrifugal separation in a state in which the pestle remains in the tube was employed so as to separate and recollect the adhesion object after homogenization, and (iii) a reaction volume in cDNA synthesis treatment after homogenization was reduced.

Specifically, the present invention is as follows:

[1] A method of sampling a plant tissue section, comprising the steps of:

inserting a first gel layer into a needle;

arranging a plant tissue on a second gel layer; and passing the needle through the plant tissue together with the second gel layer, and sampling a section of the plant tissue in the needle.

[2] The method according to [1], wherein the needle has a syringe structure.

[2-2] The method according to [1] or [2], wherein the needle has four tips arranged in a square shape.

[2-3] The method according to [1] or [2], wherein the needle has an outer diameter of 0.26 mm or less, and an inner diameter of 0.13 mm or less.

[2-4] The method according to [1] or [2], wherein the needle is of 27 gauges or 31 gauges.

[3] The method according to [1] or [2], wherein the gel layer contains a polysaccharide gel.

[4] The method according to any of [1] to [3], wherein the gel layer is a gel containing at least 1% agarose.

[5] The method according to any of [1] to [4], wherein the gel layer is a layer having a thickness of at least 1 mm.

[5-2] The method according to any of [1] to [5], wherein a sum of a thickness of the first gel layer, a thickness of the second gel layer, and a thickness of the plant tissue is adjusted to a predetermined thickness.

[6] The method according to any of [1] to [5], further comprising transferring the plant tissue section sampled in the needle into a liquid droplet.

[7] The method according to [6], wherein the liquid droplet is 1 µl or less.

[8] The method according to [6] or [7], further comprising freezing the liquid droplet.

[8-2] The method according to [8], wherein a time until transferring the plant tissue section sampled in the needle into the liquid droplet, and freezing the liquid droplet is 3 minutes or less, and preferably 1 minute or less.

[9] A method of separating a nucleic acid from a plant tissue, comprising the steps of:

disrupting a cell of a plant tissue section sampled by the method according to any of [1] to [8]; and separating a nucleic acid.

[10] The method according to [9], wherein the disruption of the cell is performed by homogenization using a pestle in a tube.

[10-2] The method according to [10], wherein the pestle has a shape which can be subjected to centrifugal separation integrally with the tube after the homogenization.

[10-3] The method according to [10], wherein the pestle has a shape which can be subjected to centrifugal separation in a state in which a tip of the pestle is completely inserted into the tube.

[10-4] The method according to [10], wherein a surface of the pestle is subjected to hydrophilic treatment.

[11] A method of producing a plant tissue-derived nucleic acid library, comprising the step of immobilizing a nucleic acid separated from a plant tissue by the method according to [9] or [10], or a nucleic acid having an identical or complementary sequence to the nucleic acid to a solid phase carrier.

[12] A method of analyzing a plant tissue-derived nucleic acid, comprising the step of analyzing a nucleic acid separated from a plant tissue by the method according to [9] or [10].

[13] A system for sampling a plant tissue section, comprising:

a sampling needle;

a means for inserting a first gel layer into the sampling needle;

a second gel layer, on which a plant tissue is to be arranged; and a mechanism for moving the sampling needle to pass through the plant tissue together with the second gel layer.

[13-2] The system according to [13], wherein the sampling needle has a syringe structure.

[13-3] The system according to [13-2], wherein the syringe structure has a plunger as a hollow small tube.

[14] The system according to [13], further comprising:

a tube containing a liquid droplet, into which the plant tissue section is to be discharged; and a liquid droplet freezing means.

[15] A system for separating a nucleic acid from a plant tissue section, comprising:

a tube containing a liquid droplet, into which a plant tissue section is inserted;

a liquid droplet freezing means; and a pestle, wherein the pestle has a shape which can be subjected to centrifugal separation integrally with the tube.

The present specification encompasses the contents described in the specification and/or drawings of JP Patent Application No. 2012-037593 based on which the present patent application claims priority.

Effect of the Invention

By the present invention, a method and a system for sampling a section from a plant tissue are provided. Also provided are a method and a system for separating nucleic acids from a plant tissue. In accordance with the present method and system, site-specific gene expression analysis of the plant tissue is enabled. This is effective for studies on action of an external stimulus to plants, site dependency of a response thereto, spatial distribution characteristics of gene expression, or the like.

DETAILED DESCRIPTION OF THE INVENTION

Figure 1:
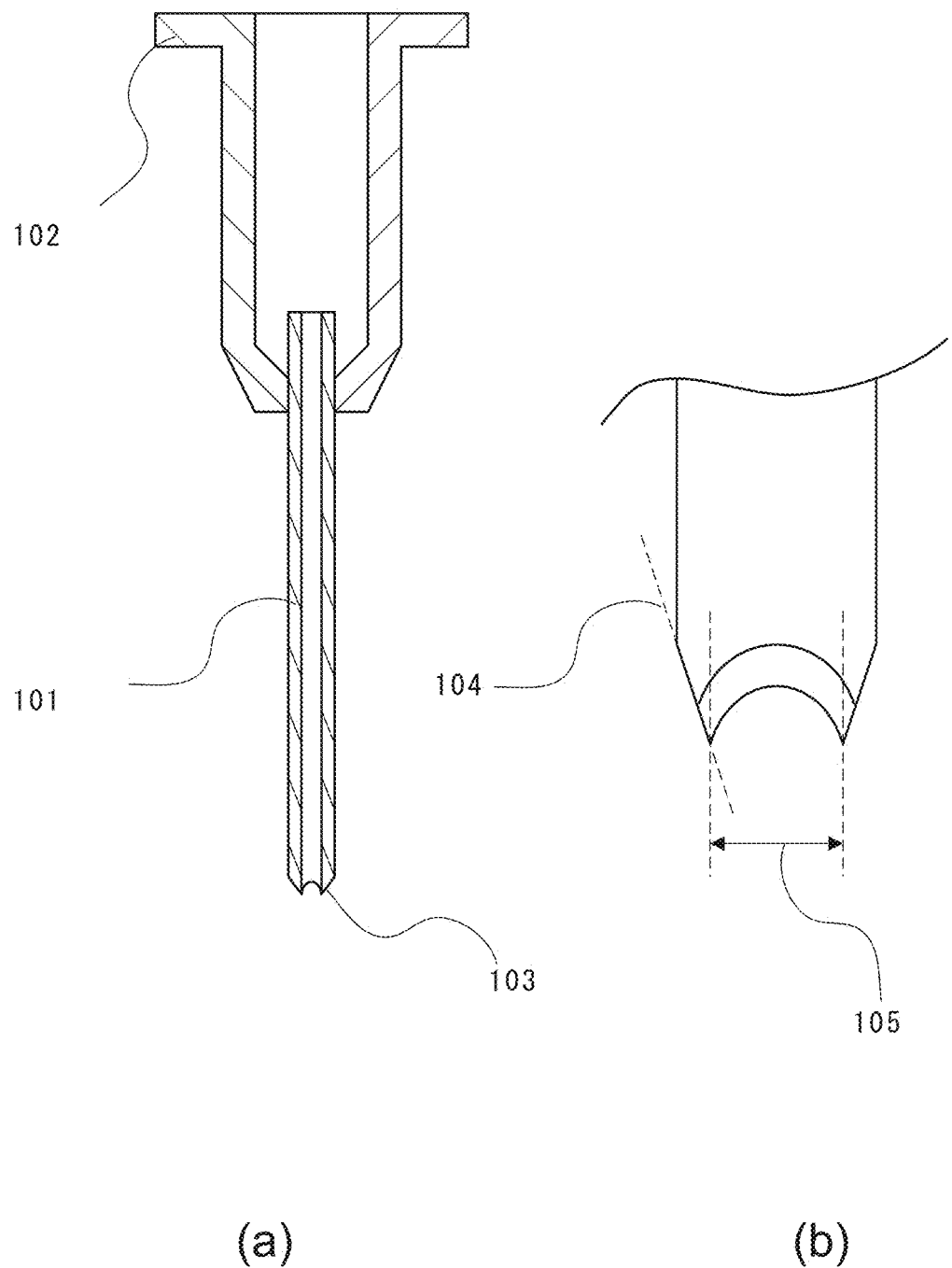
FIG. 1 illustrates one example of a plant tissue section sampling needle.

The present invention will be described in detail as follows.

The present invention provides a method and a system for sampling a section from a plant tissue, and separating nucleic acids from the obtained plant tissue section.

In the present invention, "plant" of the plant tissue, from which the section is to be sampled, means all kinds of organisms classified into plants, and specifically means organisms having cell walls and performing photosynthesis. More specifically, examples thereof include spermatophytes, pteridophytes, bryophytes, and multicellular algae. The plant tissue may be any tissue collected from such plants, and, for example, may be a tissue obtained from organs such as roots, leaves, stems, vascular systems, buds, flowers, and seeds. The obtained plant tissue may be directly used, or may be also subjected to pretreatment (washing, cutting, or the like). The "section" to be sampled indicates a small section of the plant tissue, and is preferably as small as possible, for example, 0.5 mm or less on a side.

The method of sampling the plant tissue section according to the present invention contains a step of inserting a first gel layer into a needle, and a step of arranging a plant tissue on a second gel layer. Either step may be performed first, or the steps may be performed simultaneously. The "gel layer" is a layer of gel with a certain thickness. The gel is not particularly limited as long as the gel is made of a material having an appropriate hardness for protecting the plant tissue, and not affecting components contained in the plant tissue. Examples thereof include polysaccharide gels, particularly agar gel, agarose gel and sepharose gel, and polymer gel. When production of a nucleic acid library or nucleic acid analysis is performed as described below, the gel is preferably made of a material not affecting reactions such as capture to a solid phase carrier, and cDNA synthesis (reverse transcription reaction). The hardness and the thickness of the gel layer differ depending on the size of the needle to be used, the type of the plant tissue to be sampled, or the like, and can be appropriately adjusted by a person skilled in the art. For example, when the agarose gel is used, the gel preferably contains at least 1% by weight agarose. It is preferable to use a gel containing at least 1.5% by weight, preferably 1.5 to 2% by weight, of agarose when a leaf is selected as the plant tissue, and at least 3% by weight, preferably 3 to 4% by weight, of agarose when a stem is selected. The thickness is at least 1 mm, for example, 1 mm to 5 mm, and preferably 1 mm to 2 mm.

The types, the hardnesses, and the thicknesses of the first gel layer and the second gel layer may be the same as, or different from each other. The sum of the thickness of the first gel layer, the thickness of the second gel layer, and the thickness of the plant tissue may be adjusted to a predetermined thickness. The thickness can be appropriately adjusted according to the type of the plant tissue to be sampled, the size of the needle, or the like.

The needle (a sampling needle) is not particularly limited as long as the needle has a strength and a size suitable for sampling a section from the plant tissue. For example, a commercially-available injection needle made of stainless steel may be used after being processed, if necessary. As a preferable size, a needle of 27 gauges or 31 gauges may be used. A small-size needle can sample a tissue fragment. For example, when an injection needle of 27 gauges is used, the injection needle has an outer diameter of 0.4 mm, an inner diameter of 0.2 mm, and a wall thickness of 0.1 mm, and can sample a section with about 26 cells/layer. Also, for example, when an injection needle of 31 gauges is used, the injection needle has an outer diameter of 0.26 mm, an inner diameter of 0.13 mm, and a wall thickness of 0.06 mm, and can sample a section with about 11 cells/layer.

The shape of a needle tip of the needle is not particularly limited either. For example, a circular, oval, quadrangular, or rhombus shape may be employed. It is preferable to employ a needle having four tips arranged in a square shape. Accordingly, variations in the amount of the sampled plant tissue can be suppressed. The needle having four tips also has an effect to suppress variations in the amount of sampled tissue when a section is sampled from an animal tissue as well as the plant tissue. Particularly, the needle can be used when a section is collected from a micro region in one portion of a pathological section or the like produced by freezing or formalin fixation.

The needle also preferably has a syringe structure. For example, the syringe structure may be achieved by inserting a small tube (a hollow small tube) into the needle, and using the small tube as a plunger (a pusher) for discharging a section. Accordingly, the plant tissue section sampled in the needle can be discharged easily and without being damaged. Also, the needle may be connected to a plunger by a fitting such as a luer lock, or may be held in a holder in a mechanical pencil-like shape.

The needle may be treated with a nuclease inhibitor (e.g., an RNase inhibitor) before use, so that degradation of nucleic acids in the plant tissue section can be prevented. The needle may be also treated with a hydrophilic polymer before use, so that the gel layer and the plant tissue section are easily held in the needle.

To insert the first gel layer into the needle, any method, such as a method of passing the needle through a gel sheet more than once, and a method of putting a solution in the needle and gelatinizing the solution, may be employed.

The arrangement of the plant tissue on the second gel layer is also not particularly limited, and may be performed by placing the plant tissue on a gel sheet, or by putting the plant tissue in a vessel containing a solution and gelatinizing the solution. Another gel layer may be also arranged on the plant tissue. In this case, the first gel layer may be inserted, or may not be inserted into the needle in advance.

Subsequently, a step of passing the needle through the plant tissue together with the second gel layer, and sampling a section of the plant tissue in the needle is performed. Accordingly, the plant tissue section can be sampled in a state sandwiched between the first gel layer and the second gel layer in the needle. The needle may be preferably passed as perpendicular as possible to the plant tissue and the second gel layer.

As described above, the plant tissue section can be sampled quickly, preferably within 5 minutes. The obtained plant tissue section has a micro size, and the tissue is protected.

The plant tissue section sampled in the needle may be transferred into a liquid droplet and frozen as quickly as possible. For example, a time until the plant tissue section is transferred into a liquid droplet and frozen is set to 3 minutes or less, preferably 1 minute or less. Accordingly, a gene expression state less affected by a physical stimulus during sampling can be fixed.

The liquid droplet may be prepared by pure water, saline, phosphate buffered saline (PBS), TE buffer, or a solution obtained by adding a nuclease inhibitor (e.g., an RNase inhibitor) to these solvents. Particularly, a reagent basically containing an ammonium sulfate component (a representative product name: RNALater (Ambion Inc.)), and a guanidine-based preservative solution and extraction reagent (a representative product: buffer RLT and buffer RLC (QIAGEN)) can be used as the solution supplemented with the nuclease inhibitor.

The size of the liquid droplet differs depending on the size of the sampled section. The size is preferably 1 µL or less, and for example, may be 0.5 µL. Particularly, when the solution supplemented with the nuclease inhibitor is used as the liquid droplet, the component thereof possibly inhibits cDNA synthesis. Thus, the size of the liquid droplet is preferably a minimum required size. The liquid droplet as described above may be prepared in, for example, a tube, and the plant tissue section may be transferred thereto. A tube of any type and any size that is known in the art can be used as the tube in which the liquid droplet is prepared. For example, when gene expression analysis described below is performed, a PCR tube can be employed. The tube may be preferably made of a material where the liquid droplet and the contents (nucleic acids or the like) of the plant tissue section are easily held, or treated such that the liquid droplet and the contents (nucleic acids or the like) of the plant tissue section are easily held. For example, the tube may be made of a hydrophilic material (e.g., a hydrophilic polymer), or hydrophilic treatment (e.g., coating with a hydrophilic polymer, and a UV ozone treatment method) may be performed on the surface of the tube.

The liquid droplet may be frozen after transferring the plant tissue section to the liquid droplet. The liquid droplet may be frozen by a known method in the art. For example, a method of using liquid nitrogen, and use of a freezer are generally employed. By freezing, a gene expression status within the plant tissue section can be preserved, and disruption of cells described below can be also easily performed.

Next, a method of separating nucleic acids from the plant tissue section sampled as described above is to be described. First, the cells of the plant tissue section sampled by the method of the present invention are disrupted. The disruption of the plant cells can be performed by any known method in the art, and physical disruption, e.g., homogenization using a pestle, glass beads, or ultrasonication, may be employed.

When the homogenization of the plant cells is performed using a pestle, the pestle may have a shape which can be subjected to centrifugal separation integrally with the tube after homogenizing the cells of the plant tissue section in the tube in a preferable embodiment. More preferably, the pestle may have a shape which can be subjected to centrifugal separation in a state in which its tip is completely inserted into the tube. For example, the pestle and the tube can be integrated by using a cap capable of fixing the pestle to the tube. A specific example is shown in Example 1 and FIGS. 8 to 10. Alternatively, the pestle and the tube can be integrated by using a stopper, by which the pestle is integrated with the tube and located in the center of the tube without being displaced horizontally. By performing the centrifugal separation by use of the pestle having such a shape, the contents (nucleic acids or the like) of the plant tissue section can be efficiently collected even when the contents adhere to the surface of the pestle, and a quick operation is enabled.

The pestle is also preferably made of a material to which the nucleic acids or the like of the plant tissue section do not adhere, or is treated such that the nucleic acids or the like of the plant tissue section do not adhere. For example, when the pestle is produced from a water-repellent material (e.g., polyetheretherketone (PEEK), and polyvinylidene chloride), hydrophilic treatment (e.g., coating with a hydrophilic polymer, and a UV ozone treatment method) may be performed on the surface of the pestle. Accordingly, the adhesion of the nucleic acids or the like of the plant tissue section to the pestle surface can be prevented, and the recovery rate of the nucleic acids of the plant tissue section can be further improved.

After the cell disruption, the nucleic acids derived from the plant tissue section are separated. Examples of the type of the separated nucleic acid include genomic DNA, messenger RNA (mRNA), non-coding RNA (ncRNA), micro RNA, and their fragments. The nucleic acids can be separated by using a known method in the art according to the type of the nucleic acid to be separated. For example, the nucleic acids, i.e., DNA and RNA, contained in the cells can be extracted by using a proteolytic enzyme such as Proteinase K, a chaotropic salt such as guanidine thiocyanate and guanidine hydrochloride, a surfactant such as Tween and SDS, or a commercially-available cell lysis reagent. Genomic DNA may be fragmented by, for example, physical fragmentation or restriction enzyme fragmentation. When RNA (mRNA or the like) is separated, DNA among the nucleic acids extracted as described above is degraded by a DNase, so that a sample containing only RNA as a nucleic acid is obtained. When cDNA is prepared, only mRNA may be captured by using a DNA probe containing a poly T sequence from the sample containing only RNA. After that, cDNA can be synthesized from mRNA by performing a reverse transcription reaction using a reverse transcriptase.

In accordance with the configuration of the present invention, the nucleic acids contained in the plant tissue section can be quickly and efficiently separated. This is effective in analyzing the gene expression status of a plant.

Figure 13:
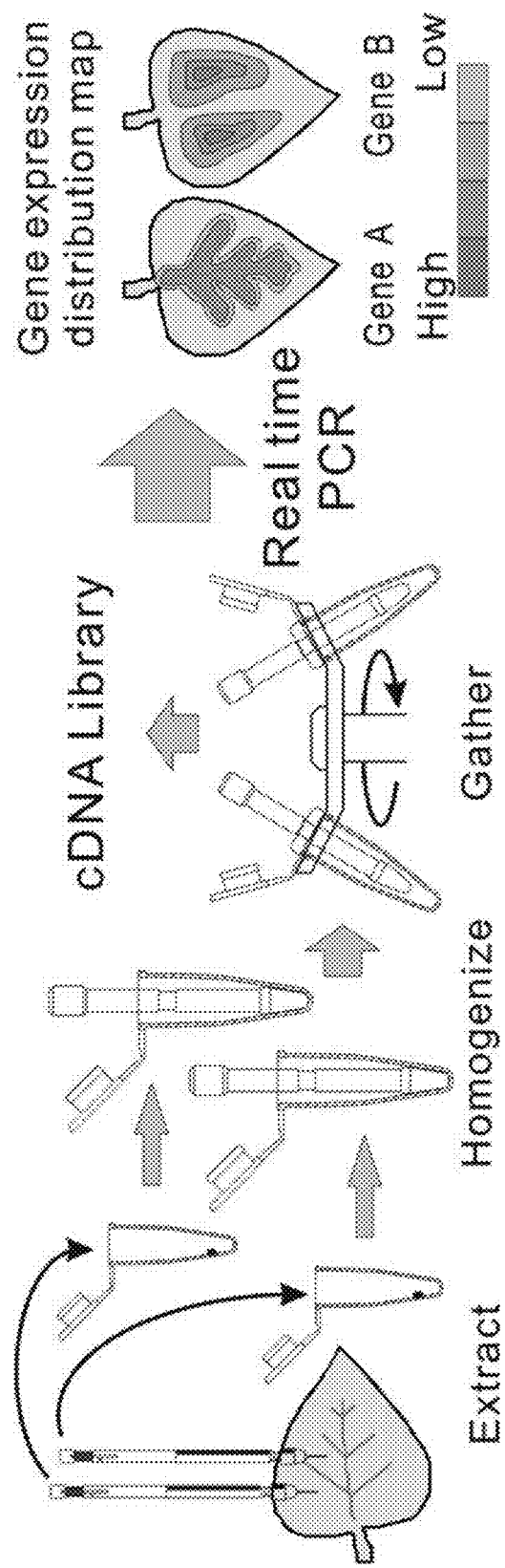
FIG. 13 is a view for explaining a process from the sampling of the plant tissue section to separation and analysis of nucleic acids.

The nucleic acids (e.g., genomic DNA, and mRNA) separated from the plant tissue as described above, or the nucleic acids (e.g., cDNA) having an identical or complementary sequence to the above nucleic acids are immobilized to a solid phase carrier, so that a plant tissue-derived nucleic acid library can be produced. Also, by analyzing the nucleic acids separated from the plant tissue as described above (or the nucleic acids immobilized to the solid phase carrier), the plant tissue-derived nucleic acids can be analyzed. The method of producing the nucleic acid library, and the method of analyzing the nucleic acids are well known in the art. For example, a library of plant tissue-derived cDNA can be produced on beads as a solid phase carrier, and nucleic acids (genes) expressed in the plant tissue can be repetitively analyzed by using methods described in Patent Document 1 and Non Patent Document 4. A specific example is shown in FIG. 13. By sampling a section from at least one position (preferably, a plurality of positions) from the plant tissue, separating nucleic acids from each section, producing a cDNA library corresponding to the nucleic acids derived from each section, and analyzing the nucleic acids by quantitative PCR in accordance with the present invention, an expression status of at least one type of gene at a certain position (or a plurality of positions) of the plant tissue can be analyzed. As described above, according to the present invention, the plant tissue-derived nucleic acids can be quickly and efficiently used.

Moreover, the present invention relates to a plant tissue section sampling system for carrying out the method as described above. Specifically, the plant tissue section sampling system of the present invention may comprise:
a sampling needle;
a means for inserting a first gel layer into the sampling needle;
a second gel layer, on which a plant tissue is to be arranged; and
a mechanism for moving the sampling needle to pass through the plant tissue together with the second gel layer.

The sampling needle is as described above, and preferably has a syringe structure. The means for inserting the first gel layer into the sampling needle may be a mechanism for moving the sampling needle to pass through a gel sheet. Alternatively, the means may be a means capable of injecting a solution that can be gelatinized into the sampling needle and gelatinizing the solution.

The first gel layer, and the second gel layer on which the plant tissue is arranged are as described above.

The mechanism for moving the sampling needle to pass through the plant tissue together with the second gel layer is also not particularly limited, and a known mechanism in the art may be used.

The present system may further comprise a means for adjusting the sum of the thickness of the first gel layer, the thickness of the second gel layer, and the thickness of the plant tissue to a predetermined thickness. The sum of the thicknesses may be adjusted to a predetermined thickness in consideration of the type of the plant tissue to be sampled, the size of the sampling needle or the like.

The plant tissue section sampling system of the present invention may further comprise: a tube containing a liquid droplet, into which the plant tissue section is to be discharged; and a liquid droplet freezing means. Accordingly, a process from the sampling of the plant tissue section to preservation of a gene expression status can be easily and quickly performed.

The plant tissue section sampling system of the present invention may further comprise an information inputting means (a camera, an observation stage, a monitor or the like) for determining a section sampling place on the plant tissue, a means for determining the position of the sampling needle, a means for moving the sampling needle and adjusting the position of the sampling needle, and a means for washing the sampling needle.

Furthermore, the present invention relates to a system for separating nucleic acids from a plant tissue section. The system may comprise:
a tube containing a liquid droplet, into which a plant tissue section is to be inserted;
a liquid droplet freezing means; and
a pestle having a shape which can be subjected to centrifugal separation integrally with the tube.

The tube containing the liquid droplet is as described above. As the liquid droplet freezing means, a freezer, liquid nitrogen or the like may be employed. The pestle is also as described above.

The nucleic acid separating system of the present invention can easily, quickly, and efficiently separate the nucleic acids from the plant tissue section.

EXAMPLES

The specific examples of the embodiments of the present invention are explained with reference to drawings as follows. It should be noted that these examples are merely examples for realizing the present invention and are not intended to limit the present invention.

Example 1

FIG. 1 shows an example of a plant tissue section sampling needle used in the present invention. A needle of 27 gauges or 31 gauges is used as a needle 101. An upper portion 102 can be connected to a plunger or the like by a luer lock similarly to an injection needle. Needle tip 103 in a lower portion is processed to four tips in a substantially square shape by cutting the tips from all quarters. FIG. 1(b) is an enlarged view of a tip portion.

The angle of cutting is indicated by 104. The needle of 27 gauges has an inner diameter (105 in FIG. 1) of about 0.21 mm, and the needle of 31 gauges has an inner diameter of about 0.13 mm. A stainless-steel small tube having an outer diameter of 0.10 mm or an outer diameter of 0.05 mm is inserted into the needle so as to provide a plunger function, and is used as a plunger (a pusher). The angle of cutting is preferably 8° to 30°. Particularly, in the case of 12° to 20°, the needle is effectively inserted into a tissue, effectively cuts a section, and also has excellent durability. In the case of a normal injection needle, an angle of 8° to 12° is used. Although the object of the present invention can be also achieved by these angles, there are problems with repetitive use since the tip with an acute angle is vulnerable to wear and deformation. Therefore, the angle of 12° to 20° is more preferable as the angle in consideration of the durability.

Figure 2:
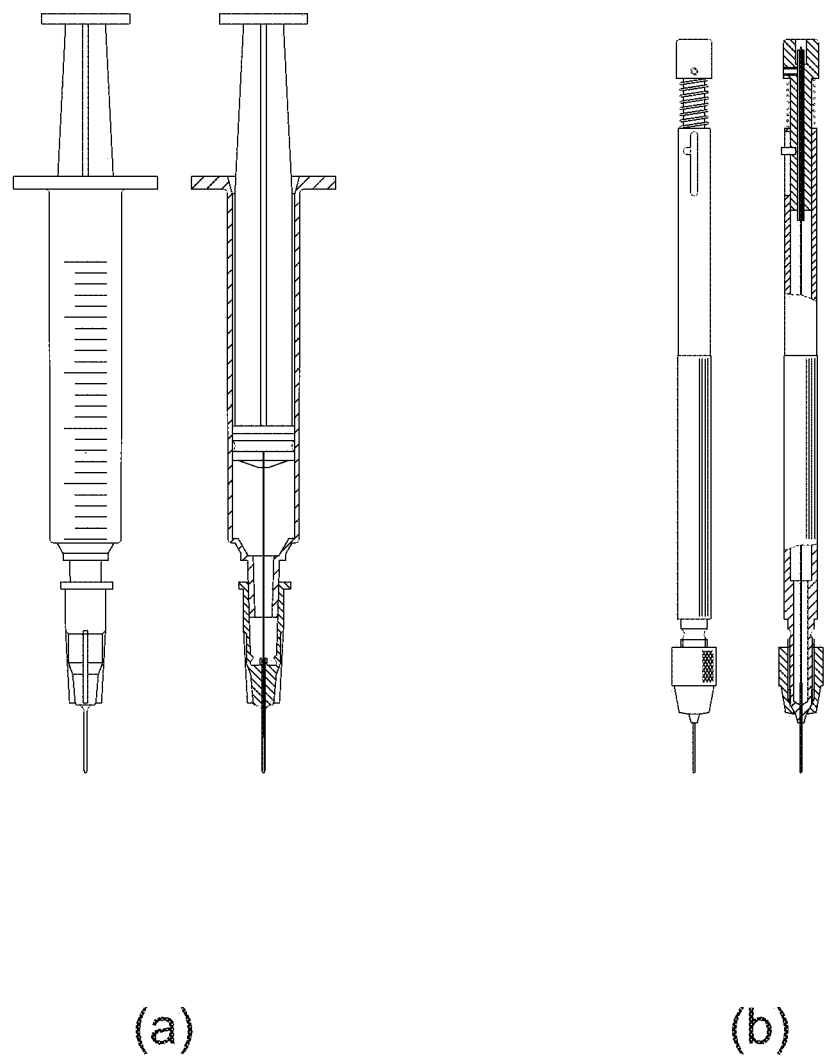
FIG. 2 are views for explaining examples of a holder of the needle.

FIG. 2(a) shows a state in which the needle is connected to a component that is separately produced experimentally to be like an injector. By moving up and down a plunger-like component of the injector, the stainless-steel small tube in the needle can be moved up and down. FIG. 2(b) shows an example of a case in which the needle is produced experimentally to be like a lead of a mechanical pencil, and is held.

Figure 3:
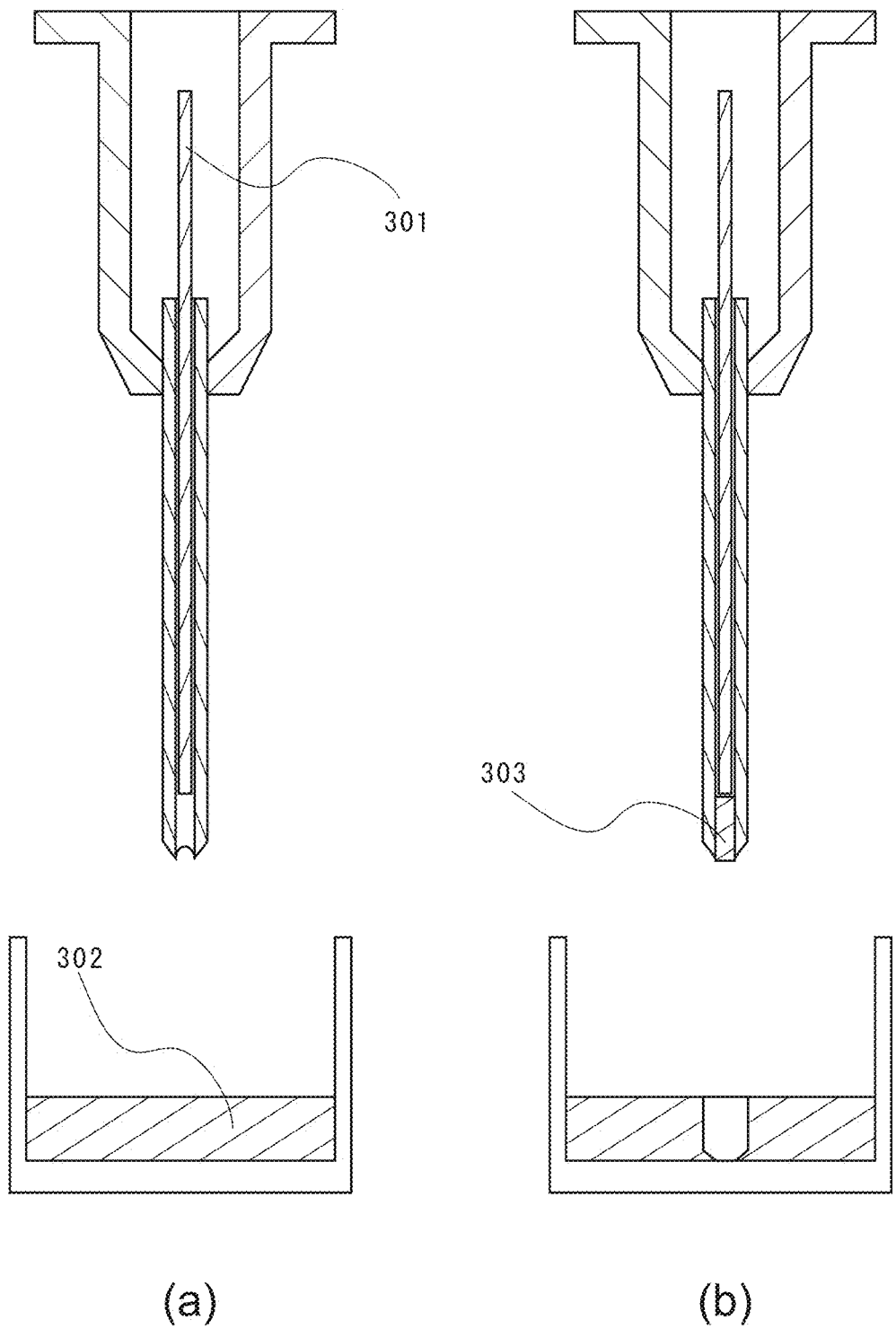
FIG. 3 are views for explaining a procedure for inserting a gel layer into the needle.

A method of using the needle is described. FIG. 3(a) shows a state in which a small tube 301 is inserted into the needle. When the needle is inserted into a gel sheet 302, a gel layer (an upper gel layer) 303 can be formed within the needle as shown in FIG. 3(b). Alternatively, the gel layer can be a gel layer previously formed by a polymer or the like. However, when gene amplification or reverse transcription reaction described below is performed, a material inhibiting these reactions, for example, silicone rubber should not be used.

Figure 4:
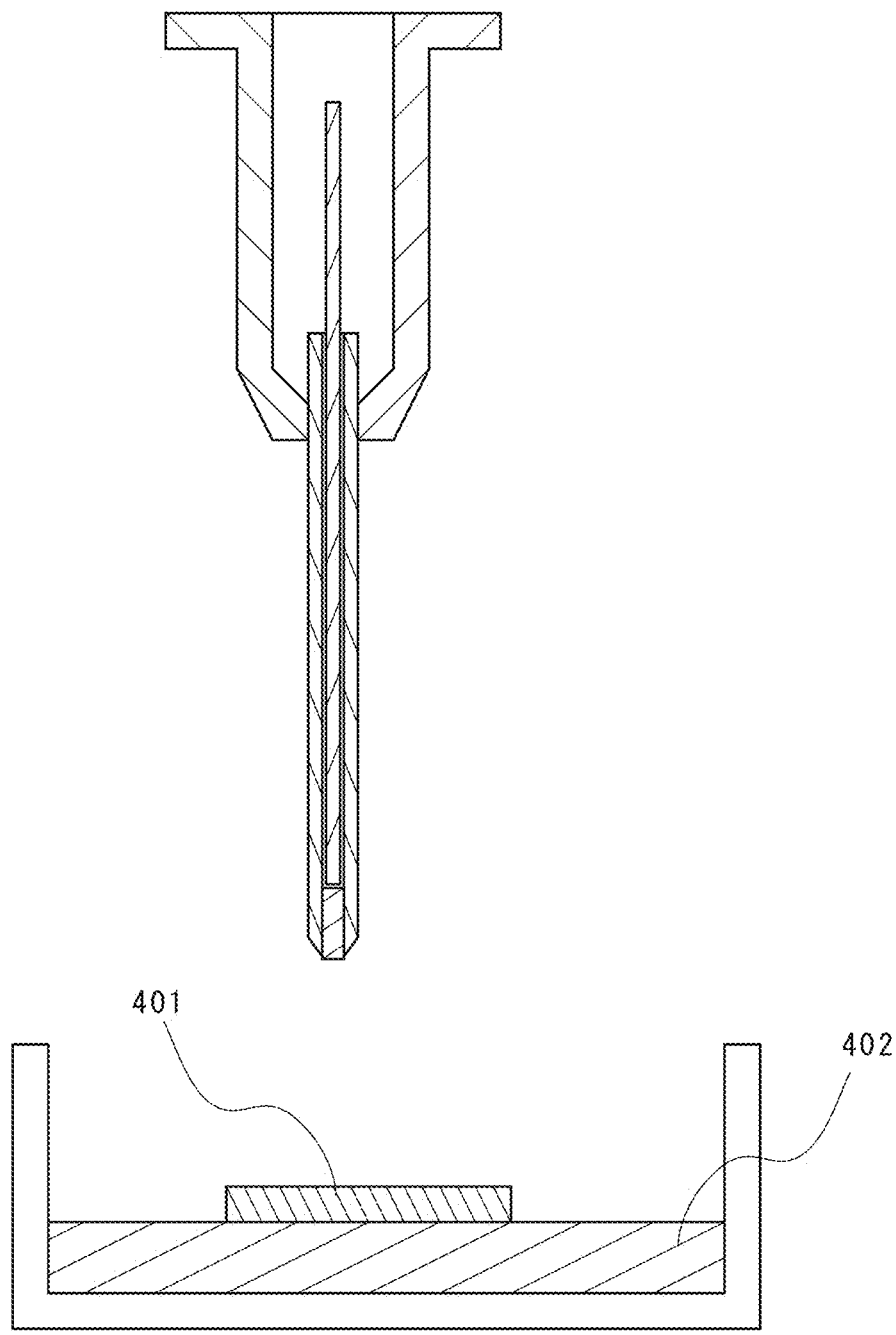
FIG. 4 is an explanatory view of a state in which a plant tissue section is sampled.
Figure 5:
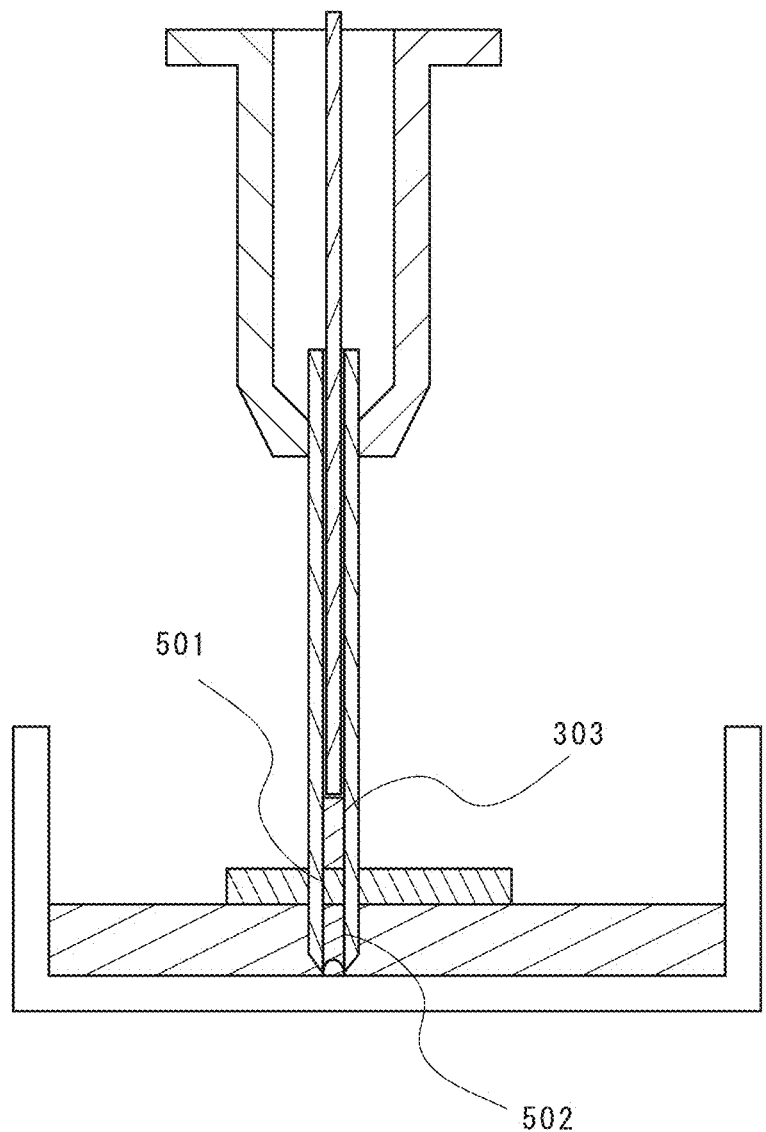
FIG. 5 is an explanatory view of a state in which the plant tissue section is sampled.
Figure 6:
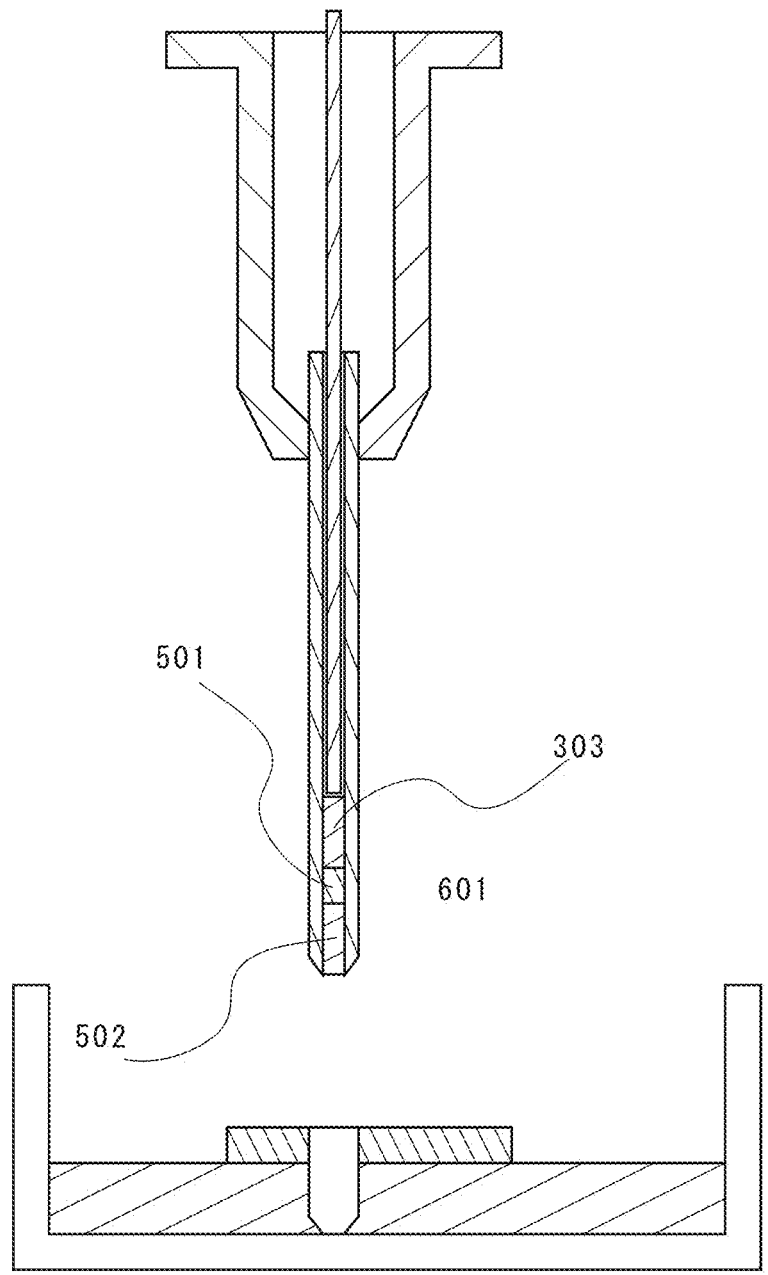
FIG. 6 is an explanatory view of a state in which the plant tissue section is sandwiched between two gel layers, and collected.

Next, sampling of a plant tissue is performed. FIGS. 4 to 7 are explanatory views for sampling a tissue section. First, a plant 401 to be sampled is arranged on a gel sheet 402 as shown in FIG. 4. In this state, the needle is stuck into the plant and a gel sheet under the plant as shown in FIG. 5. As a result, a plant tissue layer 501 and a lower gel layer 502 are inserted into the needle at a position under the above gel layer (the upper gel layer) 303. The needle is then gently pulled up, so that a sample 601 in which the gel, the tissue, and the gel described above are in a sandwich formation can be obtained within the needle. Accordingly, a micro plant tissue fragment can be sampled quickly and without being excessively stimulated (in a protected state).

Figure 7:
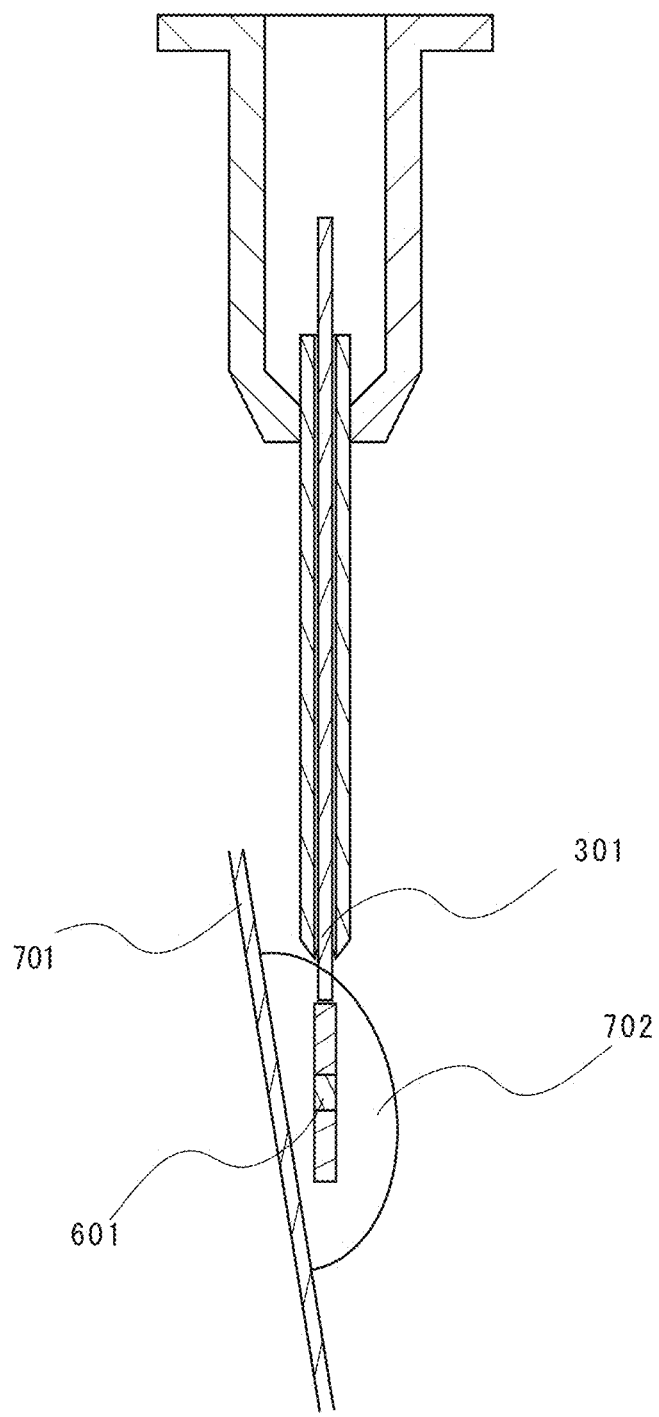
FIG. 7 is an explanatory view of a state in which the plant tissue section is transferred into a liquid droplet.

Subsequently, as shown in FIG. 7, the sample 601 can be transferred into a liquid droplet 702 that has been previously formed on an inner wall of a tube 701 by pushing out the small tube 301. In this case, since the gel layer 303 protects the section, the section can be transferred into the liquid droplet without being damaged. It may be important to use the liquid droplet when transferring the sample into the tube. If the sample is attached to the inner wall of the tube without using the liquid droplet, it is difficult to surely move the sample since the handled sample has a micro size, and cannot be observed with the naked eye. By using the liquid droplet, the tissue section pushed out by the tip of the small tube can be surely moved into the liquid droplet.

Example 2

A step of destroying cell walls and obtaining cell content in the tissue sampled in Example 1 is described. When the sample is a plant fragment as in the present example, it is generally difficult to destroy the cell walls and extract the cell content with respect to every cell in the section. As a practical method therefor, cooling to liquid nitrogen temperature and homogenization are used in the present example. When the liquid droplet is cooled to the liquid nitrogen temperature, the liquid droplet becomes an ice droplet. By homogenizing the ice droplet with a pestle, the tissue in the ice droplet can be also disrupted. However, in order to surely homogenize the ice droplet, it may be important to set the size of the liquid droplet to 1 μl or less. If the liquid droplet is larger than this size, the ice droplet has a higher strength as an object and becomes difficult to homogenize. Although it is not impossible to homogenize the ice droplet with large size by means of mechanical contrivance, the size of the liquid droplet may be set to 1 μL or less so as to manually perform a simple experiment.

Preferably, 0.5 μl of PBS is used.

Figure 8:
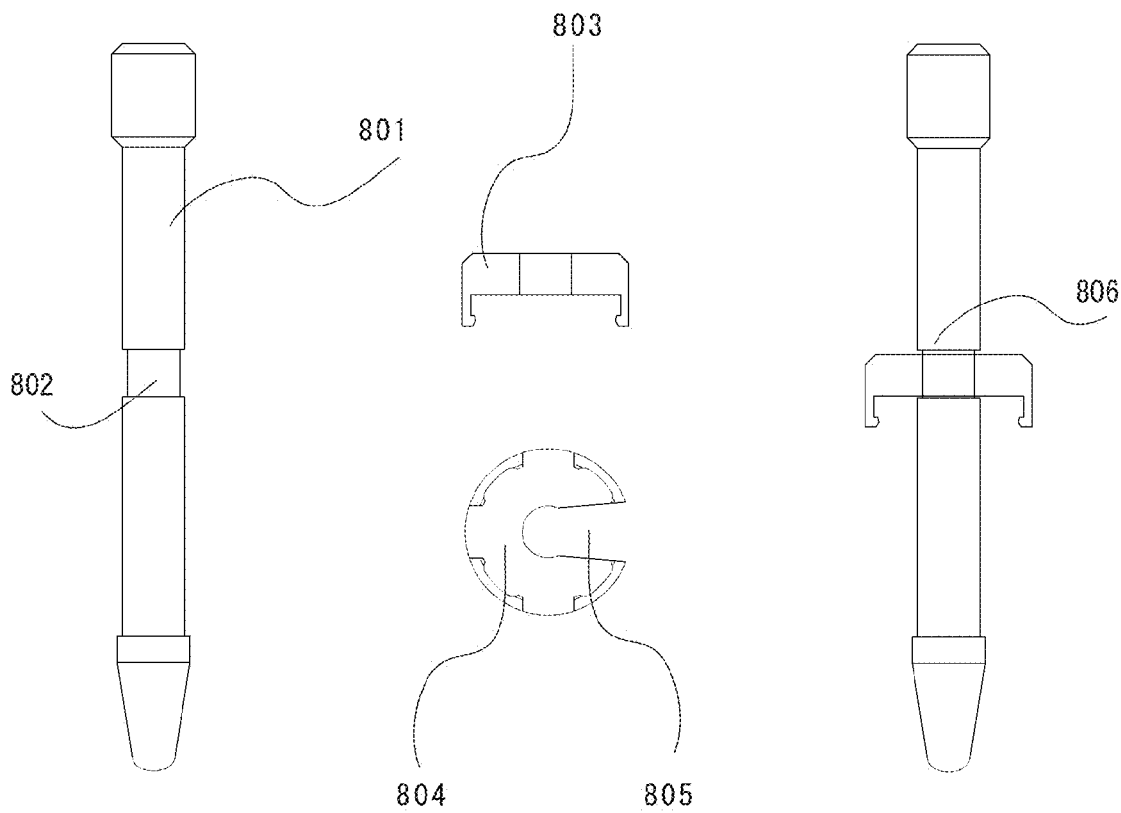
FIG. 8 illustrates one example of a pestle that can be subjected to centrifugal separation integrally with a tube.
Figure 9:
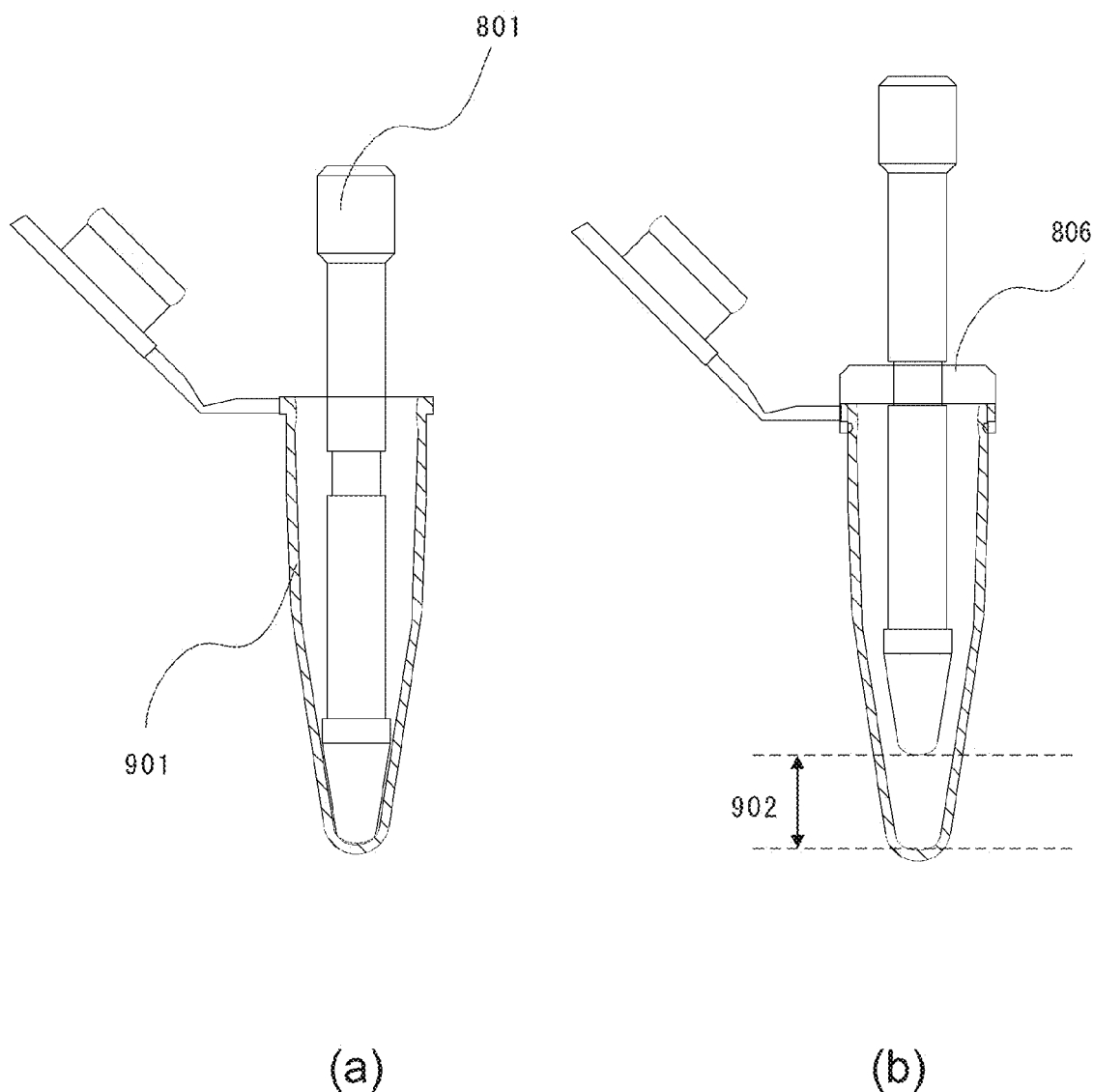
FIG. 9 are explanatory views of a state in which the pestle that can be subjected to centrifugal separation integrally with the tube is integrated with the tube.

The pestle used for homogenization also requires special contrivance. In the present example, the pestle and the tube are contrived so as to be put in a centrifuge together such that the cell content on the pestle surface can be also completely recovered after the homogenization. FIG. 8 is an explanatory view of the pestle. According to the present example, the pestle is composed of a pestle body 801 and a pestle cap 803.

The pestle body has a portion 802 where the pestle cap is fitted. Reference numeral 804 illustrates a state as viewed from the lower surface of the pestle cap. A cutout 805 is formed in the cap, so that the cap is connected to the portion 802 of the pestle. Reference numeral 806 illustrates a state in which the cap is fitted. The pestle is designed such that a lower portion of the pestle is in close contact with an inner wall of a tube 901 as shown in FIG. 9(a), so that the sample in the tube can be homogenized. Subsequently, by fitting the pestle cap (806), the pestle is integrated with the tube as shown in FIG. 9(b). At this point, a distance 902 between the lowest point of the tube inner wall and the pestle tip is set to 2 mm in the present example.

Figure 10:
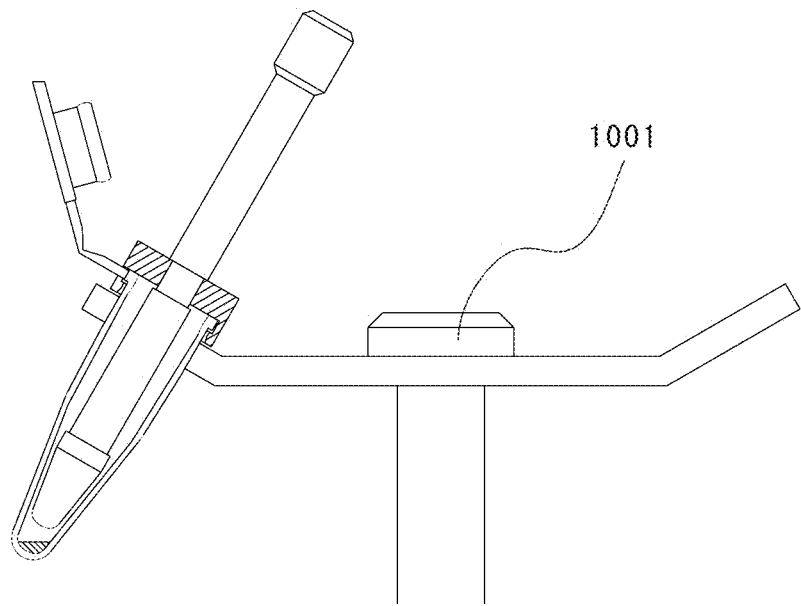
FIG. 10 is an explanatory view of a state in which the pestle that can be subjected to centrifugal separation integrally with the tube is arranged in a centrifugal separator.

FIG. 10 shows a state in which the pestle and the tube are mounted to a centrifugal separator 1001. By performing centrifugal separation in this state (a tube on the other end for maintaining a balance is omitted), the cell content adhering to the pestle surface can be recovered in the tube. Accordingly, the cell content can be efficiently recovered from the tissue fragment. In the present example, a pestle which is suitable for a 0.2 ml PCR tube was produced experimentally from a material, such as UPE: Ultra High Molecular Weight Polyethylene, PP: Polypropylene, POM: Polyoxymethylene, PPS: Polyphenylenesulfide, and PEEK: Polyetheretherketone. As a result, a pestle using PEEK had a highest recovery rate. The recovery rate is considered to indicate a rate at which the cell content adhering to the pestle surface is recovered by centrifugation.

Example 3

Next, an example of sampling a tissue section from a cotyledon of a seedling of *Arabidopsis thaliana* (wild-type col strain) after passage of 21 days from seeding as the sample, and performing gene expression analysis is described below.

1. Preparations

First, in the present example, an example of sampling the tissue section in a state sandwiched by agarose gel is described. The following preparations are performed.

(1) Agarose gel with a concentration of 2% by weight is produced using ultrapure water in a sterilized state, dispensed into a petri dish so as to form a gel sheet having a thickness of about 2 mm, and cooled to 4° C.

(2) A needle and a pestle are treated with an RNase inhibitor and dried. After that, a hydrophilic polymer is infiltrated therein, and dried.

(3) A hydrophilic polymer is also infiltrated into an inner wall of a 0.2 mL PCR tube, and dried.

(4) A liquid droplet of about 0.5 μL of a PBS aqueous solution is formed on the wall surface of the above tube, and cooled to ice temperature.

(5) Liquid nitrogen is prepared.

2. Sampling of a Tissue Section (1) The needle is mounted to a holder, and a small tube is inserted into the needle. After that, the needle is inserted into the agarose gel sheet, so that a gel layer is formed in the needle.

(2) A plant to be sampled is arranged on the gel sheet, and the needle is inserted into a sampling site. The needle is passed through the plant and the gel sheet under the plant at the same time. As a result, a test specimen in which the gel layer, the plant tissue layer, and the gel layer are in a sandwich form can be sampled in the needle.

(3) The test specimen in a sandwich form within the needle is immediately pushed out by a plunger, and transferred to the liquid droplet in the 0.2 mL tube. A lid of the tube where the test specimen is transferred is closed, and the tube is immediately immersed in the liquid nitrogen so as to cool the liquid droplet containing the test specimen. When a plurality of sites are sampled at the same time, the above operation is repeated.

3. Tissue Disruption/Homogenization (1) The tube is removed from the liquid nitrogen, and the ice droplet containing the test specimen is homogenized by the pestle (about 5 seconds). The 0.5 μL of ice droplet can be easily homogenized together with the test specimen therein.

(2) A pestle cap is fitted, and the tube is subjected to centrifugation together with the pestle (about 10 seconds).

(3) The pestle is removed from the tube, the lid is closed, and the tube is immersed in the liquid nitrogen again. When a plurality of sites are sampled at the same time, the above operation is repeated.

4. Production of cDNA Library

To produce a cDNA library, the method described in Patent Document 1 or Non Patent Document 4 is used. The method is specifically described below.

(1) First, a master Mix having the following composition is prepared (the amount per tube is described).

| Resuspension Buffer | 1.0 μl |
|---|---|
| Lysis Enhancer | 0.1 μl |
| 10x DNase I Buffer | 0.36 μl |
| DNase I | 0.5 μl |
| PBS pH 7.4 | 1.5 μl |

The above Mix is dispensed (3.96 μL after dispensation), and treated at room temperature for 5 to 10 minutes.

(2) EDTA (2.5 mM) is injected in an amount of 1.2 μL, and the resultant Mix is treated at 70° C. for 5 minutes and ice-cooled.

(3) The following reagents are added.

| 0.1% Tween20, 10 mM Tris-HCl (pH 8.0) | 15.6 μl |
|---|---|
| 10 mM dNTP Mix | 1.0 μl |
| Origo(dT)$_{30}$ magnetic beads | 1.0 μl |

(which is obtained by previously fixing origo(dT)$_{30}$ to magnetic beads)

The resultant Mix is reacted at 70° C. for 5 minutes, and cooled to 4° C.

(4) Reverse transcription is performed by using the following reagents.

| 5x RT Buffer | 6.0 μl |
|---|---|
| 0.1M DTT | 1.0 μl |
| RNase OUT | 1.0 μl |
| Super Script III RT | 1.0 μl |

The resultant Mix is stirred at 50° C. for 50 minutes to cause reaction, treated at 85° C. for 1.5 minutes, and ice-cooled.

(5) 1.0 μL of RNase H is added, and the resultant Mix is stirred at 37° C. for 30 minutes to cause reaction, and ice-cooled.

The cDNA library can be synthesized on the beads through the above process.

Figure 11:
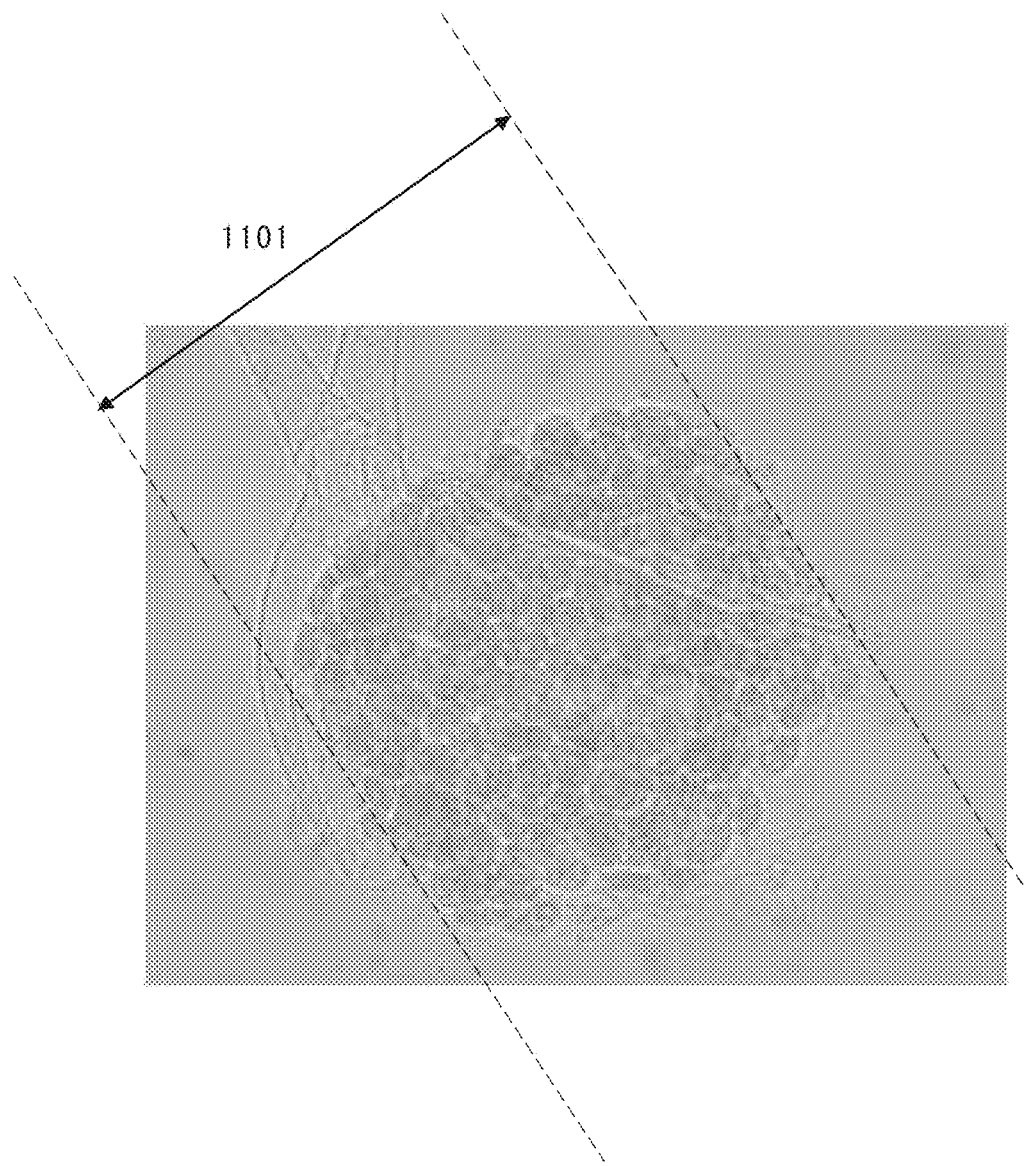
FIG. 11 shows a microphotograph of a plant tissue section sampled using a needle of 27 gauges.
Figure 14:
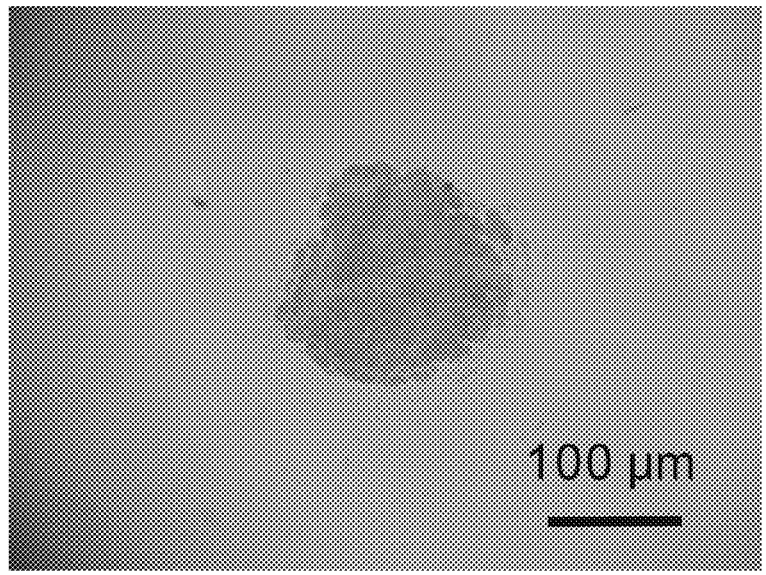
FIG. 14 shows a microphotograph of a plant tissue section sampled using a needle of 31 gauges.

FIG. 11 shows one example of the section of *Arabidopsis thaliana* sampled according to the present example. This is an example in which the needle of 27 gauges was used. As shown in FIG. 11, a tissue (about 4 μg) of about 200 μm (1101 in FIG. 11) on a side can be sampled. FIG. 14 shows an example in which the needle of 31 gauges was used. In this case, a tissue (about 2 μg) of about 150 μm can be sampled. Variations in the size at the time of sampling were about 10% or less.

To study the recovery rate of synthesized cDNA, the recovery rate was examined using primers shown in Table 1 by employing an *Arabidopsis thaliana* TUB2 (AT5G62690) gene as a standard. Since the TUB2 (AT5G62690) is expected to have a stable expression level as a housekeeping gene, the TUB2 (AT5G62690) can be used as a standard. Quantitative PCR was performed by the following method. First, control used for concentration calibration of the quantitative PCR was obtained by PCR synthesis by using "TUB2 Con FW" and "TUB2 Con RV" as primers with a cDNA solution of *Arabidopsis thaliana* as a template. By using the control, quantitative PCR analysis regarding the TUB2 was performed by using "TUB2 PCR FW" and "TUB2 PCR RV" as amplifying primers, and "TUB MGB" as an MGB probe.

As a result of the experiment, about 10,000 to 12,000 copies of TUB2 gene were recovered from the section of 200 μm. Since the cotyledon section used herein was about 4 μg, the recovery amount of the TUB2 is calculated as $2.5 \times 10^6$ to $3.0 \times 10^6$ copies/mg.

Next, when the TUB2 genes were similarly recovered by collecting a few mg of cotyledon having the same conditions by a conventional method, it was found that about $10^7$ copies were expressed per 1 mg as the gene dosage. Therefore, it is calculated that about 25 to 30% of expressed genes can be recovered by the technique of the present example.

Also, in the experiment using the needle of 31 gauges, the collected section was about 2 μg, and the TUB2 recovery amount was about $1.9 \times 10^6$ copies/mg of genes. Thus, it indicates that the recovery rate in the gene recovery using the needle of 31 gauges is about 19%. The reason why the recovery rate is lower than that of using the needle of 27 gauges is assumed to be that the section to be collected is smaller.

Figure 15:
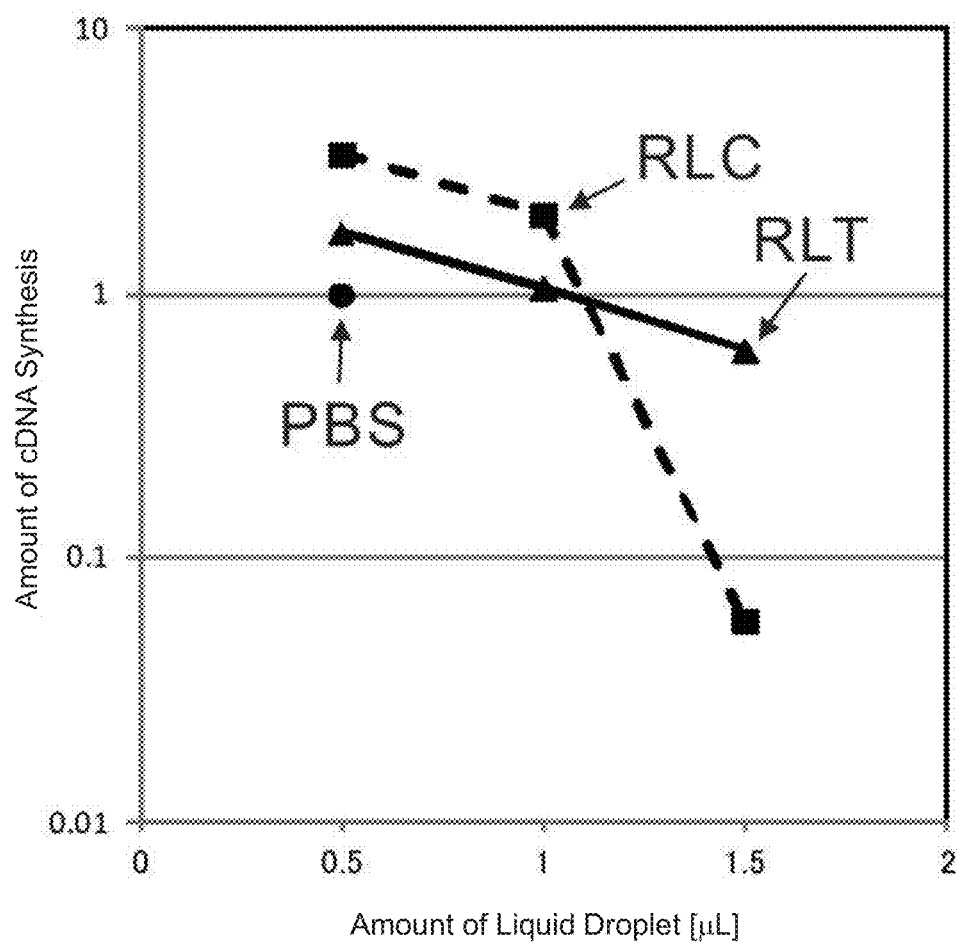
FIG. 15 is a graph showing the result of comparing the amount of cDNA synthesis with respect to the amount of a liquid droplet when the needle of 31 gauges is used by employing buffer RLT and buffer RLC, which are reagents containing a nuclease inhibiting component, as a reagent used for the liquid droplet.

Here, to further improve the gene recovery rate, a reagent other than the PBS was also studied as the reagent used for the liquid droplet. Use of buffer RLT and buffer RLC (both QIAGEN), which are examples of the reagent having a nuclease inhibiting component, as the liquid droplet was studied. The experiment was performed using the needle of 31 gauges. FIG. 15 shows a result of comparing the amounts of cDNA synthesis with respect to the amount of a liquid droplet. The result is shown by normalizing the case in which the PBS is used to 1. Accordingly, the following conclusion was obtained. When the RLT and the RLC were used, the amounts of cDNA library synthesis were respectively improved about 1.7 times and 3.4 times on the condition of 0.5 μL. To the contrary, when the amount of liquid droplet was increased, the amounts of cDNA library synthesis were lowered. This is because the nuclease inhibiting component of the reagent functions to inhibit cDNA synthesis. Accordingly, it has been found that it is important to decrease the amount of the liquid droplet to minimum necessity when the reagent having the nuclease inhibiting component is used. From the above results, it has been found that the recovery rate and the cDNA synthesis rate of the expressed genes can be improved to about 60% or more by optimizing the liquid droplet.

Moreover, in the tissue sampling using the needle, the effect of rapidity in the operation from sampling the tissue section into the needle to transferring the tissue section into the liquid droplet in the tube was evaluated. In the present example, the operation from the sampling using the needle to the discharge into the tube can be completed within about 10 to 15 seconds. Thus, during the operation, the tissue section was discharged into the tube after an interval of a certain time after the sampling, and the amounts of cDNA library synthesis from the samples were compared, so that the result in FIG.

Figure 16:
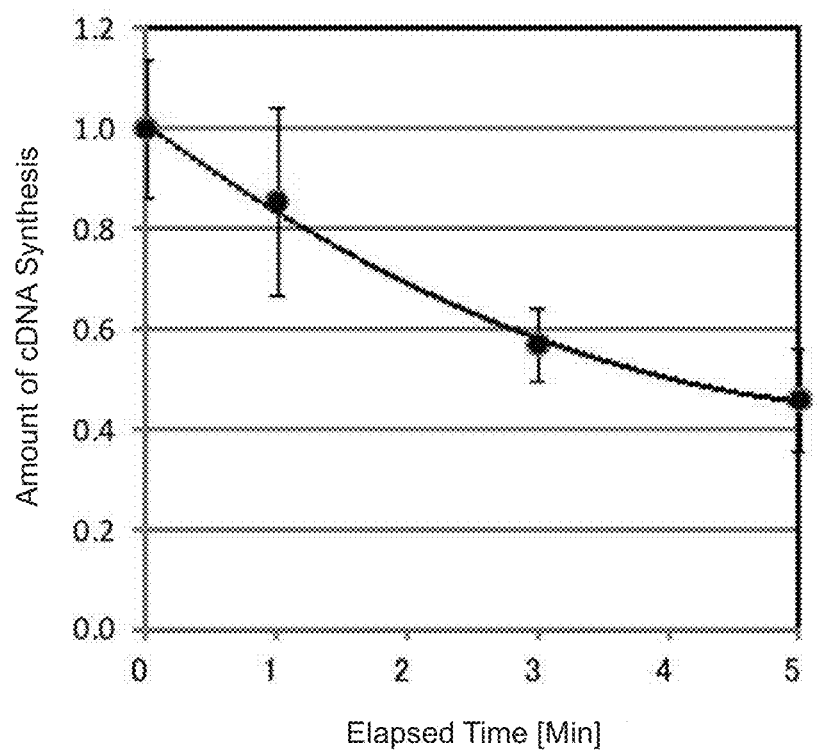
FIG. 16 is a graph showing the result of comparing the amounts of cDNA library synthesis from samples obtained by discharging the tissue section into the tube with an interval of a certain time provided after the sampling using the needle.

16 was obtained. FIG. 16 shows the amounts of cDNA synthesis according to the provided intervals (elapsed times) by setting the operation with no interval to zero minutes. The result is shown by normalizing the zeroth minute to 1. Accordingly, it is found that the recovered gene amount decreases when it takes longer for sampling, and is reduced to about half when it takes 3 to 5 minutes. In a conventional technique, when a section is sampled by a laser or the like, it takes longer until recovery as the section becomes smaller. Thus, the gene recovery rate is lowered. The technique of the present example enables gene recovery while avoiding gene degradation.

TABLE 1

Primers and Quantitative PCR Primer for TUB2 Gene

| Name | Seq (5'→'3') | SEQ ID NO: |
|---|---|---|
| TUB2 Con FW | CAAGGCACGGACGCTAC | 1 |
| TUB2 Con RV | GAAACATCACAGGCAATAACA | 2 |
| TUB2 PCR FW | TGAATATCAACAGGAGGAAGAGTA | 3 |
| TUB2 PCR RV | GTGTTCCTTTTAAAAAAAGAAAAGT | 4 |
| TUB MGB | TGTTTTGTTTTAAAGCAGTTATA | 5 |

Example 4

Figure 12:
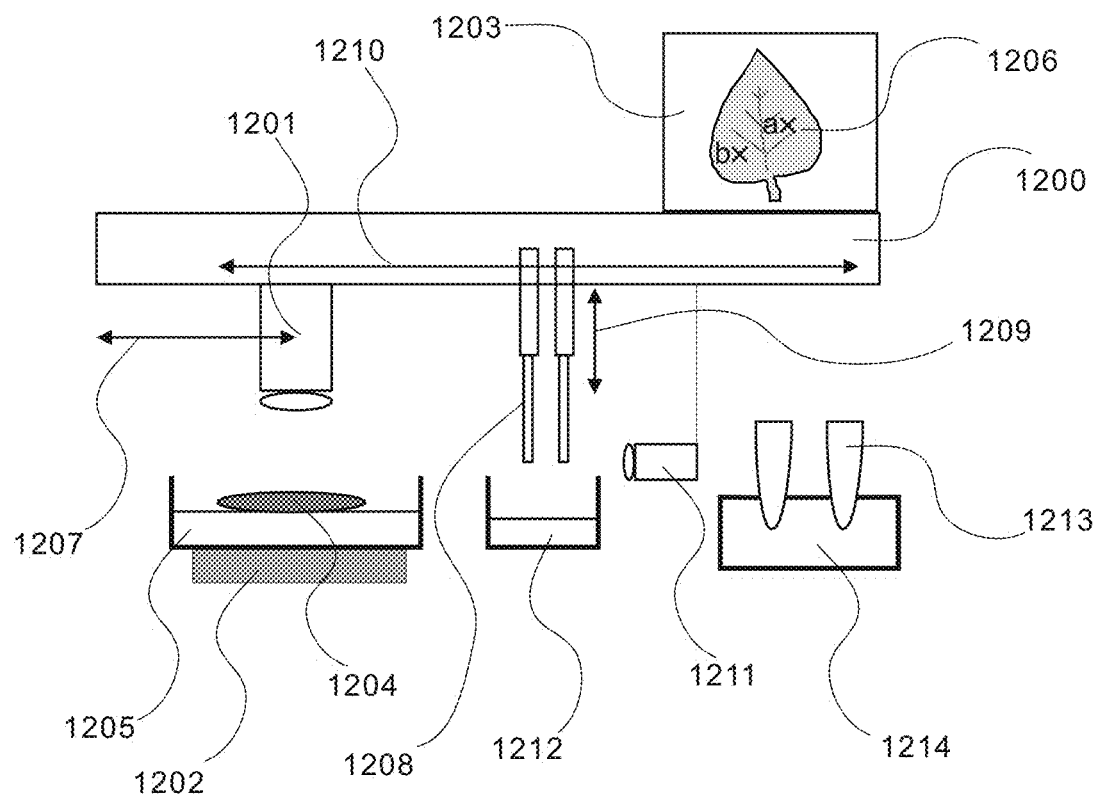
FIG. 12 illustrates one example of a sampling system of the plant tissue section.

In the present example, a section sampling system is described based on FIG. 12. A sampling system 1200 comprises an information inputting means for previously determining a sampling place while observing a target plant in a microscope observation image or the like, a sampling means for inserting a gel into the tip of a sampling needle, sampling a tissue, and discharging the tissue to a tube or the like based on the information, and a cooling means for cooling the temperature of the tube or the like. Since the sampling means can be respectively independently controlled, the system can continuously sample tissues at a plurality of sites.

First, the information inputting means is described. The information inputting means comprises a microscope camera 1201 that takes an image of a plant to be sampled, a microscope observation stage 1202, and a monitor 1203 that displays the image. First, a user places a sampling target plant 1204 on the microscope observation stage 1202. At this time, the plant 1204 is placed on and fixed to a gel sheet 1205. The user designates a sampling position on an observation image 1206 (a and b in FIG. 12) by position designation inputting means such as a pointer after adjusting the focus of the microscope image. The system thereby calculates and records the height and the horizontal position of the sampling designated position in the target plant 1204 on the stage 1202. Particularly, with regard to the height information, it is important to measure and calculate a distance from the position of the plant body to the lower surface of the gel sheet. When a plurality of sections are to be sampled, the position designation is repeated. The microscope camera 1201 is moved in a horizontal direction 1207 to a position not disturbing the sampling when the plant section is sampled.

Next, the sampling means is described. The sampling means comprises a sampling needle 1208, and a means for moving the needle in a vertical direction 1209 and a horizontal direction 1210. First, the sampling needle 1208 is connected as a preparation. The sampling needle is connected by an injection needle-like connector in one example, and the sampling needle is held like a mechanical pencil in another example. In both examples, the needle, in which a plunger small tube is inserted, is connected and fixed to the sampling means. After connecting the needle 1208, the needle tip position (height) is measured. This is to control the position of a needle tip of the sampling means such that the needle is passed through the gel sheet in a lower portion, and the needle tip is not damaged by a vessel under the gel sheet when the plant section is sampled. The needle tip position can be easily measured by image recognition by observing the needle tip with a camera 1211 from the horizontal direction. When a system user gives an operation instruction after setting the sampling position for the plant 1204 on the stage 1202, the sampling means automatically samples the plant section at the sampling position. In the following, the operation process is specifically described. When a user inputs a sampling operation start signal, the sampling means first passes the needle through a sheet-like gel 1212 to form a gel layer in the needle. Subsequently, the needle tip position is moved to a position vertically above the sampling position. The needle tip may be located at a position about 0.5 mm above the plant at the sampling position. However, since it is necessary to prevent previous contact between the needle and the plant as the necessary condition, a distance larger than the above distance may be employed in consideration of a position measurement error. Subsequently, the needle 1208 is pushed vertically downward, and passed through the plant tissue 1204 so as to reach the gel sheet 1205 under the plant tissue 1204. After that, the needle 1208 is moved up, so that the tissue section can be sampled in the needle. Subsequently, the needle tip is moved to a portion vertically above a liquid droplet in a previously-prepared tube 1213, and the small tube in the needle is pushed out to push the sampled section to the outside of the needle. After that, the pushed-out section is brought into contact with the liquid droplet, so that the section moves to the liquid droplet. The tube 1213 is cooled by cooling means 1214 to keep the liquid droplet at about 0 to 4° C. After moving the tissue section, the tube 1213 is moved to another cooling means to be immediately cooled by liquid nitrogen. The sampling is completed through the above operation. Although the needle can be washed by disengaging the needle itself from the sampling means, the needle may also be washed by passing a washing solution from the small tube in the needle as an easier method.

All publications, patents, and patent applications cited herein are incorporated herein by reference in their entirety.

DESCRIPTION OF SYMBOLS

101 Needle
102 Needle Upper Portion
103 Needle Tip
104 Angle of Cutting
105 Needle Inner Diameter
301 Small Tube
302 Gel Sheet
303 Upper Gel Layer
401 Plant
402 Gel Sheet
501 Plant Tissue Layer
502 Lower Gel Layer
601 Sample
701 Tube
702 Liquid Droplet
801 Pestle
802 Portion where Pestle Cap is Fitted
803 Pestle Cap
804 Pestle Cap
805 Cutout 806 Pestle where Pestle Cap is Fitted
901 Tube
902 Distance between Lowest Point of Tube Inner Wall and Pestle Tip
1001 Centrifugal Separator
1101 One Side of Sampled Tissue
1200 Sampling System
1201 Microscope Camera
1202 Microscope Observation Stage
1203 Monitor
1204 Plant
1205 Gel Sheet
1206 Observation Image
1207 Horizontal Direction
1208 Sampling Needle
1209 Vertical Direction
1210 Horizontal Direction
1211 Camera
1212 Gel
1213 Tube
1214 Cooling Means

SEQUENCE LISTING FREE TEXT

SEQ ID Nos. 1 to 5: Artificial Sequence (Primer)

The invention claimed is:

1. A method of sampling a plant tissue section, comprising the steps of:
   inserting a first gel layer into a needle;
   arranging a plant tissue on a second gel layer; and
   passing the needle through the plant tissue together with the second gel layer, and sampling a section of the plant tissue in the needle.

2. The method according to claim 1, wherein the needle has a syringe structure.

3. The method according to claim 1, wherein the needle has an outer diameter of 0.26 mm or less, and an inner diameter of 0.13 mm or less.

4. The method according to claim 1, wherein the first, second, or first and second gel layer contains a polysaccharide gel.

5. The method according to claim 1, wherein the first, second, or first and second gel layer is a gel containing at least 1 to 4% agarose.

6. The method according to claim 1, wherein the first, second, or first and second gel layer is a layer having a thickness of at least 1 mm.

7. The method according to claim 1, further comprising transferring the plant tissue section sampled in the needle into a liquid droplet.

8. The method according to claim 7, wherein the liquid droplet is 1 µL or less.

9. The method according to claim 7, further comprising freezing the liquid droplet.

10. The method according to claim 1, wherein the needle has four tips arranged in a square shape.

11. A method of separating a nucleic acid from a plant tissue, comprising the steps of:
    disrupting a cell of a plant tissue section sampled by the method according to claim 1; and
    separating a nucleic acid.

12. The method according to claim 11, wherein the disruption of the cell is performed by homogenization using a pestle in a tube.

13. A method of analyzing a plant tissue-derived nucleic acid, comprising the step of analyzing a nucleic acid separated from a plant tissue by the method according to claim 11.

14. A system for sampling a plant tissue section, comprising:
    a sampling needle;
    a means for inserting a first gel layer into the sampling needle;
    a second gel layer, on which a plant tissue is to be arranged; and
    a mechanism for moving the sampling needle to pass through the plant tissue together with the second gel layer.

15. The system according to claim 14, further comprising:
    a tube containing a liquid droplet, into which the plant tissue section is to be discharged; and
    a liquid droplet freezing means.

* * * * *